United States Patent [19]

Barner et al.

[11] 4,070,450

[45] Jan. 24, 1978

[54] SUNSCREENING COMPOUND AND METHOD

[75] Inventors: Richard Barner, Witterswil; Walter Boguth, Riehen, both of Switzerland

[73] Assignee: Hoffman-La Roche, Inc., Nutley, N.J.

[21] Appl. No.: 643,427

[22] Filed: Dec. 22, 1975

Related U.S. Application Data

[63] Continuation-in-part of Ser. No. 608,957, Aug. 29, 1975, abandoned.

[51] Int. Cl.$^2$ ...................... A61K 7/42; C07D 471/00
[52] U.S. Cl. ............................... 424/59; 260/297 HP; 260/295 VB; 424/263
[58] Field of Search ................ 260/295.5 V, 295 VB, 260/295 F; 424/263, 59

[56] References Cited

U.S. PATENT DOCUMENTS

| | | | |
|---|---|---|---|
| 2,260,173 | 11/1941 | Dohrn et al. | 424/59 |
| 2,377,188 | 5/1945 | Schwenk et al. | 424/59 |
| 2,583,774 | 1/1952 | Hoffman | 260/295 VB |
| 2,955,115 | 10/1960 | Kummeron et al. | 260/295 VB |

*Primary Examiner*—Dale R. Ore
*Attorney, Agent, or Firm*—Samuel L. Welt; Bernard S. Leon; R. Hain Swope

[57] ABSTRACT

Radiation screening preparations comprising a cosmetically acceptable carrier and, as the active ingredient, one or more compounds represented by the formula

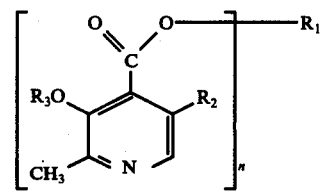

wherein $n$ is 1, $R_1$ is hydrogen, alkyl, alkali metal, ammonium or ammonium substituted with one or more alkyl or hydroxyalkyl residues, $R_2$ is hydroxymethyl or alkoxymethyl and $R_3$ is hydrogen; or $R_1$ and $R_2$ together constitute a methylene group and $R_3$ is hydrogen, methyl or ethyl; and wherein $n$ is 2, $R_1$ is an alkaline earth metal, $R_2$ is hydroxymethyl or alkoxymethyl and $R_3$ is hydrogen and pharmaceutically acceptable acid addition salts thereof. The preparations may additionally contain other agents which are characterized by a maximum light absorption in the erythemal range. Certain novel compounds are disclosed.

16 Claims, No Drawings

SUNSCREENING COMPOUND AND METHOD

This application is a continuation-in-part of Ser. No. 608,957, filed Aug. 29, 1975 now abandoned.

DETAILED DESCRIPTION OF THE INVENTION

The sunscreening preparations provided in accordance with the present invention contain as the essential active ingredient one or more substances represented by the following formula:

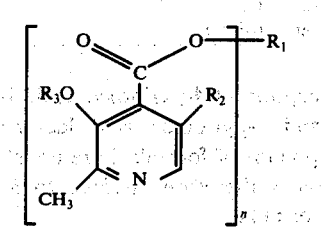

I wherein $n$ is 1, $R_1$ is hydrogen, alkyl, alkali metal, ammonium or ammonium substituted with one or more alkyl or hydroxyalkyl residues, $R_2$ is hydroxymethyl or alkoxymethyl and $R_3$ is hydrogen; or $R_1$ and $R_2$ together constitute a methylene group and $R_3$ is hydrogen, methyl or ethyl; and wherein $n$ is 2, $R_1$ is an alkaline earth metal, $R_2$ is hydroxymethyl or alkoxymethyl and $R_3$ is hydrogen.
and pharmaceutically acceptable acid addition salts thereof. The active ingredient is applied to the skin in combination with a conventional, dermatologically acceptable carrier material. Carrier materials as contemplated herein include those materials generally utilized as a base for sunscreen preparations such as, for example, creams, milks, ointments, gels, solutions, lotions, sprays, aerosols and the like. Such materials, to be suitable, must be dermatologically and cosmetically acceptable and compatible with the specific active ingredient utilized. The active ingredients of formula I are particularly advantageous in that the solubility requirements in the finished agent can be substantially taken into consideration by the choice of a certain member (e.g. a salt can be chosen for an aqueous agent).

Examples of suitable carrier materials for the formulation of the sunscreen compositions of the invention include the paraffins, waxes, vegetable or animal oils and fats such as, for example, olive oil, sesame oil, peanut oil and the like, wool fat, spermaceti, esters of fatty acids such as stearic, palmitic and oleic as well as the acids themselves, glycerides of said acids, ethyl, isopropyl, cetyl, stearyl and palmityl alcohols, emulsifying agents of all common types, e.g., nonionic, anionic or cationic suitable for the preparation of both water-in-oil and oil-in-water emulsions, thickeners such as, for example, the commercially available cellulose ethers, tragacanth, alginic acid or salts thereof and the like. Additional additives which may be incorporated into the sunscreen preparations of the invention are preservatives, buffers, pH regulators to adjust the pH thereof to approximate that of the skin, perfumes, physiologically compatible dyestuffs and the like. A preferred pH regulator in accordance with the invention is ascorbic acid.

The compounds of formula I have demonstrated a maximum specific absorption of ultraviolet light in the erythemal range, i.e., between 2900 A. and 3200 A. In addition, the compounds of formula I have been demonstrated to be compatible with the skin and are well tolerated. Of the compounds of formula I, 4-pyridoxic acid and 4-pyridoxic acid lactone are metabolites of pyridoxine (vitamin $B_6$). The remainder are derivatives of these metabolites. Therefore, in contrast to conventional ultraviolet light absorbing substances, the compounds of formula I are not foreign substances to the body.

The compounds of formula I are additionally advantageous in that they are odorless and possess good chemical and photochemical stability, thus obviating the need for additional ingredients conventionally added to sunscreening preparations to compensate for deficiencies in these properties where they exist. Further, the compounds of formula I wherein $R_3$ is hydrogen have been found to transform a large portion of the absorbed skin damaging ultraviolet light rays into long wave length fluorescent rays (420 nm). As these fluorescent rays lie within the skin tanning range, a beneficial effect is realized in addition to the shielding of the skin from the erythemal rays by the use of these compounds.

The radiation screening capability of any particular sunscreen preparation will vary with the type of vehicle utilized and the concentration of active ingredient therein. Generally, in accordance with the present invention, the concentration of the active ingredient, i.e., the one or more compounds of formula I, should be at least 1% by weight and not more than 25% by weight. Preferred preparations contain from about 2% by weight to about 6% by weight of one or more of the compounds of formula I. Wherein more than one compound of formula I is utilized in a sunscreen preparation, they may be combined in any proportion.

It is also within the scope of the present invention to combine the compounds of formula I with one or more conventional sunscreening agents. By this is meant organic compounds whose maximum light absorption lies between 2900 A. and 3200 A. This property is characteristic of many organic compounds belonging to diverse classes of compounds which are recognized in the art as sunscreens. For purposes of brevity only representative examples of such compounds will be listed hereafter. More detailed lists may be found, for example, in most recognized tests on cosmetology. Conventional light-screening agents of this type include the following:

1. Derivatives of a p-aminobenzoic acid such as, for example, esters such as ethyl, propyl, butyl and isobutyl p-aminobenzoate, ethyl p-dimethylaminobenzoate, glyceryl p-aminobenzoate, amyl p-dimethylaminobenzoate and the like;
2. Derivatives of cinnamic acid such as, for example, 2-ethoxyethyl p-methoxycinnamate, ethylhexyl p-methoxycinnamate, p-methoxycinnamic acid mixed esters and cinnamic acid mixed esters;
3. Dibenzylhydrazines;
4. Derivatives of 2-phenylbenzimidazole such as, for example, 2-phenylbenzimidazole-5-sulfonic acid;
5. Derivatives of salicylic acid such as, for example, salicylic acid menthyl ester, salicylic acid homomenthyl ester and salicylcic acid phenyl ester;
6. Derivatives of benzophenone such as, for example, 4-phenylbenzophenone, 4-phenylbenzophenone-2-carboxylic acid isooctyl ester and 5-chloro-2-hydroxybenzophenone;

7. Derivatives of coumarin such as, for example, 7-hydroxycoumarin, beta-umbelliferoneacetic acid and 6,7-dihydroxycoumarin;
8. Derivatives of gallic acid such as, for example, digalloyl trioleate;
9. Dehydroacetic acid (3-acetyl-6-methyl-1,2-pyran-2,4-dione);
10. Derivatives of quinoline such as, for example, the sodium salt of 8-ethoxyquinoline-5-sulfonic acid;
11. Derivatives of anthranilic acid such as, for example, anthranilic acid menthyl ester; and
12. Hydroxyphenylbenztriazole.

The compounds of formula I can likewise be combined with purine derivatives such as, for example, adenine or guanine or with pyrimidine derivatives such as, for example, cytosine or uracil.

In addition, the active ingredients of the light screening compositions of the invention can likewise be combined with anti-inflammatory substances such as, for example, pantothenic acid or esters thereof, phenylbutazone, azulene, azulene derivatives or azulene related substances such as Kamillen extracts and the like. Other agents which have medicinal or therapeutic value may also be incorporated in the compositions of the invention.

The compositions of the invention afford excellent protection from the erythemal rays of the sun thereby preventing painful sunburn. These compositions may be applied freely to the skin in whatever amount the user finds to be effective for the degree of protection desired. As with any conventional suntan preparation, such amounts vary with the exposure conditions, the sensitivity and pigmentation of the skin of the user and the like. Therefore, what constitutes an effective amount of the preparations of the invention is within the discretion of the user.

In accordance with the present invention, the term "alkyl" whether referring to an alkyl residue or the alkyl portion of, e.g., alkoxy or hydroxyalkyl residues indicates a straight- or branched-chain hydrocarbon residue containing up to 20 carbon atoms. Preferred are alkyl residues containing up to seven carbon atoms. By "pharmaceutically acceptable acid addition salts of the compounds of formula I" is meant salts with pharmaceutically acceptable inorganic acids such as hydrochloric acid, hydrobromic acid, sulfuric acid and the like and salts with pharmaceutically acceptable organic acids such as acetic acid, oxalic acid, lactic acid and the like.

The compounds of formula I wherein $R_2$ is hydroxymethyl or alkoxymethyl, $R_3$ is hydrogen and $R_1$ is hydrogen, alkali metal, alkaline earth metal or substituted ammonium salts are preferred. Examples of alkali metals include sodium and potassium. Suitable alkaline earth metals include, for example, calcium and magnesium. Examples of suitable substituted ammonium salts include diethanolammonium, triethanolammonium and the like. An especially preferred group of compounds in accordance with the present invention includes:
Sodium-4-pyridoxinate
Potassium-4-pyridoxinate
Triethanolammonium-4-pyridoxinate
Tris(hydroxymethyl)ammonium-4-pyridoxinate.

The wavelength (measured in ethanol) of the maximum absorption of a number of compounds preferred in accordance with the present invention is given in the following table:

TABLE

| Compound of formula I | Absorption Max. (nm) |
| --- | --- |
| 4-Pyridoxic acid | 316 |
| Sodium-4-pyridoxinate | 312 |
| Methyl-4-pyridoxinate | 320 |
| n-Hexyl-4-pyridoxinate | 328 |
| 4-Pyridoxic acid lactone-hydrochloride | 312 |
| 4-Pyridoxic acid lactone-3-methyl ether | 307 |
| Triethanolammonium-4-pyridoxinate | 312 |
| Tris(hydroxymethyl)aminomethane-4-pyridoxinate | 312 |
| 5-O-cetyl-4-pyridoxic acid | 315 |
| Sodium-5-O-cetyl-4-pyridoxinate | 311 |

With the exception of 4-pyridoxic acid, 4-pyridoxic acid lactone and 4-pyridoxic acid lactone-3-methyl ether, the compounds of formula I are novel.

The invention is therefore directed to novel compounds of the formula

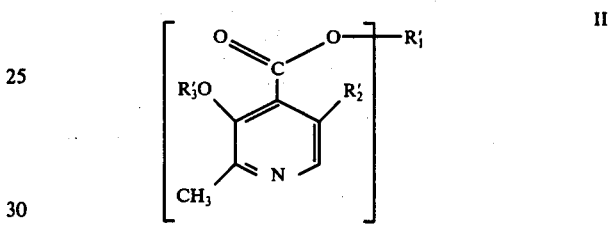

wherein $n$ is 1, $R'_1$ is hydrogen, alkyl, alkali metal, ammonium or ammonium substituted with one or more alkyl or hydroxyalkyl groups, $R'_2$ is hydroxymethyl or alkoxymethyl, and $R'_3$ is hydrogen, with the proviso that, $R'_2$ is not hydroxymethyl in case $R'_1$ is hydrogen; and $R'_1$ and $R'_2$ together are a methylene group and $R'_3$ is ethyl, and wherein $n$ is 2, $R'_1$ is an alkaline earth metal, $R'_2$ is hydroxymethyl and $R'_3$ is hydrogen
and pharmaceutically acceptable acid addition salts thereof.

The compounds of formula II and their acid addition salts can be prepared by the following methods:

a. The compounds of formula II wherein $n$ is 1, $R'_1$ and $R'_3$ are hydrogen and $R'_2$ is alkoxymethyl are prepared by oxidizing a compound represented by the formula

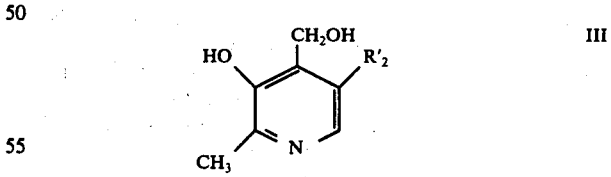

wherein $R'_2$ is alkoxymethyl to form the corresponding acid;

b. The compounds of formula II wherein $n$ is 1, $R'_1$ is alkali metal, ammonium or ammonium substituted with one or more alkyl or hydroxyalkyl residues, $R'_2$ is hydroxymethyl or alkoxymethyl and $R'_3$ is hydrogen; and wherein $n$ is 2, $R'_1$ is an alkaline earth metal, $R'_2$ is hydroxymethyl or alkoxymethyl and $R'_3$ is hydrogen, are prepared by treatment of a compound represented by the formula

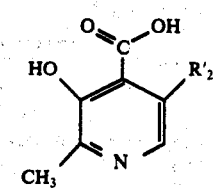

wherein $R'_2$ is hydroxymethyl or alkoxymethyl with a base represented by the formula $$R'_1(OH)_m \qquad V$$

wherein $R'_1$ is an alkali metal, ammonium or ammonium substituted with one or more alkyl or hydroxyalkyl groups and $m$ is 1 or $R'_1$ is an alkaline earth metal and $m$ is 2;

c. Compounds of the formula II wherein $n$ is 1, $R'_1$ is alkyl, $R'_2$ is hydroxymethyl or alkoxymethyl and $R'_3$ is hydrogen, or a compound of the formula IV wherein $R'_2$ has the meaning given above or a salt thereof are reacted with a compound represented by the formula $$R'_1X \qquad VI$$

wherein X is fluoro, chloro, bromo, iodo or p-toluenesulfonic acid ester and $R'_1$ is as defined above; or d. The compounds of formula II wherein $R'_1$ and $R'_2$ together are a methylene group and $R'_3$ is ethyl are prepared by the reaction of 4-pyridoxic acid lactone with diazoethane and conversion of the resulting compound to an acid addition salt of the compound of formula II, if desired.

In preparation (a) a compound of formula III is converted to the corresponding acid by oxidation.

The compounds of formula III wherein $R'_2$ is alkoxymethyl are new and can be prepared by the reaction of the known compound VII by the following reaction scheme

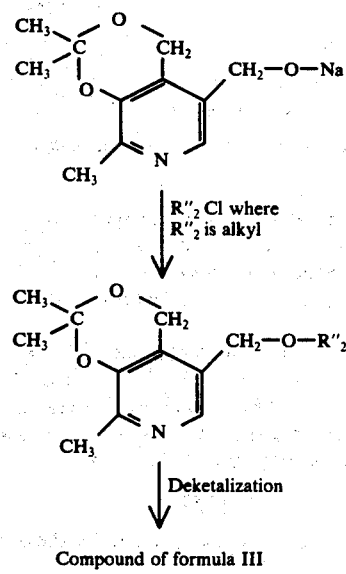

Compound of formula III

The oxidation can be carried out in analogy to the conversion of pyridoxine to pyridoxic acid as described in the Journal of Heterocyclic Chemistry, 4, 625 (1967).

In reaction (b) above, an equivalent amount of the base of the formula V is reacted with the compounds of formula IV to form the compound of formula II. The compounds of formula IV wherein $R'_2$ is alkoxymethyl are novel and can be prepared according to preparation (a) above.

In preparation (c) wherein a compound of formula IV or a salt thereof is reacted with a compound represented by the formula $R'_1X$, the reaction can be carried out preferably under basic conditions, at room temperature and in the presence of an inert or organic solvent such as, for example, dimethylformamide (DMF).

The reaction of 4-pyridoxic acid lactone with diazoethane is carried out in the presence of an inert organic solvent, e.g., methanol, utilizing an excess of an ethereal solution of diazoethane. The temperature advantageously lies between 0° and 20° C.

The present invention is further illustrated by the following examples wherein the preparation of compounds of formula II is shown as well as the incorporation thereof into specific compositions suitable as light screening preparations. All temperatures are in degrees Centigrade.

EXAMPLE 1

A total of 7.32 g (40 mmol) of 4-pyridoxic acid prepared according to the method of D. Heyl, J. American Chemical Society 70, 3434 (1948) was dissolved in 20 ml of a freshly prepared 2N aqueous solution of sodium hydroxide (40 mmol). The solution was then diluted with ethanol and evaporated almost to dryness on a rotary evaporator whereby the major portion of the water was removed by azotropic distillation. Finally, ethyl acetate was added to the reaction mixture until crystallization began. There was obtained 4.96g of the colorless sodium salt as first crystals. An additional 2.1g of product was obtained from the mother liquor after decoloration with activated charcoal. The 7.07g of sodium salt thus obtained was a hydrate. The sodium salt free of water of hydration was obtained in utilizing as the base sodium methoxide in methanol. The product had a mp of 250°–252° (decomposition) the salt is very soluble in water, soluble in alcohol and sparingly soluble in ethyl acetate.

EXAMPLE 2

A total of 1.10g (5 mmol) of the sodium salt of pyridoxic acid prepared according to example 1 were dissolved at room temperature in 15 ml of dimethyl formamide and treated dropwise with stirring with 784mg of methyliodide. After several minutes, fine crystals began to separate from the reaction mixture. After addition was completed, stirring was continued for an additional two hours afterwhich the crystals were removed by vacuum filtration. Additional crystals were obtained from the filtrate by cooling. The product was recrystallized from a mixture of equal parts methanol and water to yield 875mg of pale yellow crystals of methyl-4-pyroxinate, mp 256° (deomposition).

In an analogous manner there was obtained the n-hexyl ester of 4-pyridoxic acid utilizing n-hexyliodide at 80° for 4 hours and working up the reaction mixture with water and chloroform. The product, recrystallized from a mixture of chloroform and hexane had a mp of 154°–155°.

EXAMPLE 3

4.185 Grams (20 mmol) of 3-O-4-O-isopropyliden pyridoxine prepared as described by W. Korytnyk and M. Ikawa, Methods of Enzymology, Vol. XVIII, Part A, 527; Academic Press 1970 were reacted with 1.18g sodium methoxide in 20 ml methol and heated under reflux to yield the sodium salt which was taken up in methanol and dried at room temperature under vacuum (0.01 Torr) to yield the salt in crystalline form. The salt was dissolved in 50 ml dimethylformamide and treated dropwise with stirring with 8,426g (22 mmol) of cetyliodide. The reaction mixture was thereafter stirred at room temperature overnight (15 hours), the product mixed with water and benzene and the organic phase dried over sodium sulfate. The organic phase was then chromatographed on Kieselgel with a 1:1 mixture of benzene and ethyl acetate to yield 2.56g. of pure 3-O-4-O-isopropyliden-5-O-cetylpyridoxine as colorless crystals. The product was treated with a mixture of 10 ml dioxane and 10 ml in Hcl and heated under reflux for 90 minutes to form crystalline 5-O-cetylpyridoxine hydrochloride. Recrystallization from ethanol ether yielded 2.5 g of the hydrochloride with a melting point of 120°–122°. Oxidation of the free base (mp 91°–92°) with manganese dioxide in chloroform at room temperature over three hours gave in quantitative yield 5-O-cetyl-pyridoxal, mp 48.5°–49.5°.

One gram of the 5-O-cetylpyridoxal formed above was dissolved in a solution of 1.0g potassium hydroxide in 80 ml absolute methanol. The resulting solution was stirred with 7.0g of activated manganese dioxide for six days at room temperature. The manganese salt which had gone into solution was oxidized to manganese dioxide by the addition of 5 ml of 30% hydrogen peroxide. The hot reaction mixture was immediately filtered and the precipitated manganese dioxide washed with a solution of potassium hydroxide in methanol. The product was precipitated as the free acid by acidification of the yellow filtrate with 1N hydrochloric acid to a pH of 4. The reaction mixture was allowed to stand for 30 minutes and was then filtered through a glassfrit. The pale yellow residue was first washed with water then with ethanol and ether. The resulting 5-O-cetyl-4-pyridoxic acid was separated from residual aldehyde by dissolving in alcoholic potassium hydroxide followed by reprecipitation with 1N hydrochloric acid. There was obtained 0.41g of pure acid, mp 220° (decomposition).

EXAMPLE 4

A total of 102 mg of 5-O-cetyl-4-pyridoxic acid was treated under reflux with sodium methoxide in 5 ml of absolute methanol for 1 hour. The solvent was removed by evaporation on a rotary evaporator and the resulting sodium-5-O-cetyl-4-pyridoxinate dried overnight under high vacuum. Yield 70 mg.

EXAMPLE 5

A cream was prepared from the following formulation:

| Ingredient | Amount in Grams |
|---|---|
| Fat Phase | |
| Emulgade 1000 NI (1) | 0.5 |
| Lanette O (2) | 0.2 |
| Cetiol HE (3) | 3.0 |
| White Vaseline | 5.0 |
| Softisan 100 (4) | 15.0 |
| Softisan 601 (4) | 3.0 |
| Hydrogenated Peanut Oil | 4.0 |
| Eumulgin C 700 (5) | 4.0 |
| Dehymuls E (6) | 1.0 |
| Suitable perfume | 0.5 |
| Water Phase | |
| Dowicil 200 (7) | 0.3 |
| Sodium-4-pyridoxinate | 5.0 |
| Water | 58.5 |

(1) Saturated fatty alcohol glycol ether available from Henkel
(2) Cetylstearyl alcohol available from Henkel
(3) Fatty acid ester available from Henkel
(4) Refined hand fats available from Dynamit Nobel
(5) Saturated fatty alcohol poly glycol ether available from Henkel
(6) Mixture of high molecular weight aliphatic esters available from Henkel
(7) [1-(3-chlorallyl)-3,5,7-triaza-1-azonia-adamantan chloride] available from Dow Chemical The ingredients of the fat phase were melted together by heating to a temperature of between 45° and 50° with slow stirring. The sodium-4-pyroxinate and Dowicil 200 were dissolved in 58.5 ml of cold water, the resulting solution was warmed to between 45° and 50° and combined with the fat phase with constant stirring. The mixture was cooled to room temperature over a period of three hours with stirring. Finally, the pH of the resulting cream was adjusted to a pH 6 with ascorbic acid.

EXAMPLE 6

A cream was prepared from the following formulation:

| Ingredient | Amount in Grams |
|---|---|
| Fat Phase | |
| Emulgade 1000 NI | 2.5 |
| Cetyl Alcohol | 1.0 |
| White Vaseline | 2.0 |
| Hydrogenated Peanut oil | 2.0 |
| Glyceryl Monostearate | 1.5 |
| Diethyleneglycol Monostearate | 3.0 |
| Softisan 100 | 2.0 |
| Cremophor O (1) | 1.0 |
| Eumulgin C 700 | 1.0 |
| Cetiol HE | 1.0 |
| Water Phase | |
| Sodium Pyridoxinate | 6.0 |
| Tris - buffer solution containing 1% by weight citric acid pH 8 | 20.0 |
| A 1% by weight aqueous solution of Carbopol 940 buffered to pH 8 with tris (2) | 54.0 |
| Suitable Perfume | 0.2 |
| Panthenol Ethyl Ether | 0.5 |
| Dowicil 200 | 0.3 |
| Water | 2.0 |

(1) Alkyl-or acyl-substituted poly addition product of ethylene oxide available from BASF
(2) Carboxyl vinyl polymer of extremely high molecular weight available from Union Carbide.

The ingredients of the fat phase were combined and heated to 80° with stirring to form a homogeneous mass. The sodium pyridoxinate was dissolved in the buffer solution which was in turn combined with the Carbopol solution.

The resulting solution was blended with the fat phase at 80° and the mixture cooled with stirring. When the mixture reached 50° the remaining ingredients of the water phase were added and the mixture allowed to cool to room temperature with stirring.

EXAMPLE 7

A cream was prepared as above from the following formulation:

| Ingredient | Amount in Grams |
|---|---|
| Fat Phase | |
| Pyridoxic Acid | 5.00 |
| Triethanolamine | 8.15 |
| Propyleneglycol | 6.00 |

-continued

| Ingredient | Amount in Grams |
| --- | --- |
| Amphisol | 3.55 |
| Stearic Acid | 1.20 |
| Cetyl Alcohol | 1.20 |
| Isopropyl Myristate | 3.00 |
| Arachis Oil | 1.20 |
| Diethyleneglycol Monostearate | 1.20 |
| Purified Wool Fat | 3.55 |
| PCL-liquid (1) | 0.10 |
| Water Phase | |
| 2% by weight aqueous solution of Carbopol in water neutralized to pH 7 | 50.00 |
| Dowicil 200 | 0.20 |
| Water | 15.65 |

(1) Branched-chain fatty acid esters available from Dragoco.

EXAMPLE 8

A lotion was prepared as described below from the following formulation:

| Ingredient | Amount in Grams |
| --- | --- |
| Fat Phase | |
| Emulgade 1000 NI | 0.5 |
| Cetylstearyl Alcohol | 0.1 |
| Cetiol HE | 1.5 |
| White Vaseline | 2.5 |
| Softisan 100 | 7.5 |
| Softisan 601 | 1.5 |
| Hydrogenated Peanut Oil | 4.0 |
| Emulgin C 700 | 4.0 |
| Dehymuls E | 1.0 |
| Suitable Perfume | 0.5 |
| Water Phase | |
| Dowicil 200 | 0.7 |
| Sodium-4-pyridoxinate | 3.0 |
| Dehymuls E | 0.5 |
| Water | 71.0 |

The components of the fat phase were melted together at a temperature of between 45° and 50°. Quantities of Dehymuls E and Emulgin C given in the water phase were dissolved in 35 ml of water. At the same time, the sodium-4-pyridoxinate and Dowicil 200 were dissolved in 36 ml of water. The two aqueous solutions were combined and then mixed with the fat phase with constant stirring. The mixture was cooled to room temperature and then stirred for an additional three hours. Finally, the pH of the lotion was adjusted to a pH of 6 with ascorbic acid.

EXAMPLE 9

A gel was prepared as follows:

| Ingredient | Amount in Grams |
| --- | --- |
| Carbopol 940 | 1.20 |
| Triethanolamine | 2.50 |
| Dowicil 200 | 0.15 |
| Sodium 4-pyridoxinate | 4.00 |
| Water | 92.15 |

The Carbopol was completely dissolved in 85 ml of water, warmed to 70°. The Dowicil and triethanolamine were combined and added to the warm solution. Finally, the mixture was combined with a solution of the sodium-4-pyridoxinate at room temperature. The resultant gel had a pH of 7.2.

EXAMPLE 10

A gel was prepared in the manner given in Example 9 from the following formulation:

| Ingredient | Amount in Grams |
| --- | --- |
| Carbopol 940 | 1.20 |
| Triethanolamine | 2.50 |
| Dowicil 200 | 0.15 |
| Sodium-4-pyridoxinate | 6.00 |
| Water | 90.15 |

EXAMPLE 11

A Carbopol gel was prepared in accordance with the method given in Example 9 from the following formulation:

| Ingredient | Amount in Grams |
| --- | --- |
| Carbopol 940 | 1.8 |
| Tris(hydroxymethyl) amino methane | 3.6 |
| Water | 54.6 |

The resulting gel was added a solution prepared by dissolving the following ingredients in 33.325 g of water

| Ingredient | Amount in Grams |
| --- | --- |
| Sodium Pyridoxinate | 6.0 |
| Tris(hydroxymethyl) amino methane | 0.300 |
| Citric Acid | 0.075 |
| Dowicil 200 | 0.300 |

We claim:

1. A method of protecting skin from erythma inducing ultraviolet radiation which comprises applying to the skin an amount of a sunscreen composition sufficient for the protection thereof, said composition comprising an inert, dermatologically acceptable carrier selected from the group consisting of a cream, a milk, an ointment, a gel, a lotion, a spray and an aerosol and from about 1% by weight to about 25% by weight of an active ingredient consisting essentially of one or more compounds represented by the formula

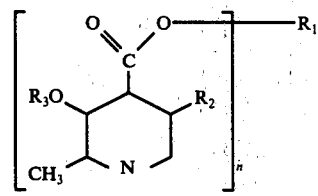

wherein $n$ is 1, $R_1$ is hydrogen, alkyl, alkali metal, ammonium or ammonium substituted with one or more alkyl or hydroxy alkyl residues, $R_2$ is hydroxymethyl or alkoxymethyl and $R_3$ is hydrogen; or $R_1$ and $R_2$ together represent a methylene group and $R_3$ is hydrogen, methyl or ethyl; and wherein $n$ is 2, $R_1$ is an alkaline earth metal, $R_2$ is hydroxymethyl or alkoxymethyl and $R_3$ is hydrogen; and pharmaceutically acceptable acid addition salts thereof.

2. A method in accordance with claim 1 wherein said active ingredient comprises from about 2% by weight to about 6% by weight of said composition.

3. A method in accordance with claim 1 wherein $n$ is 1, $R_1$ is hydrogen, alkali metal or ammonium substituted with one or more alkyl or hydroxyalkyl residues, $R_2$ is hydroxymethyl or alkoxymethyl and $R_3$ is hydrogen.

4. A method in accordance with claim 1 wherein $n$ is 2, $R_1$ is an alkaline earth metal, $R_2$ is hydroxymethyl or alkoxymethyl and $R_3$ is hydrogen.

5. A method in accordance with claim 1 wherein said active ingredient is 4-pyridoxic acid.

6. A method in accordance with claim 1 wherein said active ingredient is sodium-4-pyridoxinate.

7. A method in accordance with claim 1 wherein said active ingredient is potassium-4-pyridoxinate.

8. A method in accordance with claim 1 wherein said active ingredient is triethanolammonium-4-pyridoxinate.

9. A method in accordance with claim 1 wherein said active ingredient is 5-O-cetyl-4-pyridoxic acid.

10. A method in accordance with claim 1 wherein said active ingredient is methyl-4-pyridoxinate.

11. A method in accordance with claim 1 wherein said active ingredient is n-hexyl-4-pyridoxinate.

12. A method in accordance with claim 1 wherein said active ingredient is 4-pyridoxic acid lactone hydrochloride.

13. A method in accordance with claim 1 wherein said active ingredient is 4-pyridoxic acid lactone-3-methyl ether.

14. A method in accordance with claim 1 wherein said active ingredient is sodium-5-O-cetyl-4-pyridoxinate.

15. A method in accordance with claim 1 wherein said active ingredient is tris(hydroxymethyl)aminomethane-4-pyridoxinate.

16. A compound represented by the formula

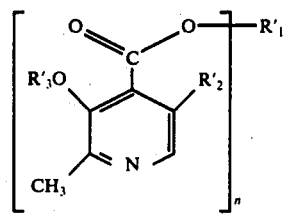

wherein $n$ is 1, $R'_1$ is hydrogen, alkyl, alkali metal, ammonium or ammonium substituted with one or more alkyl or hydroxyalkyl residues, $R'_2$ is hydroxymethyl or alkoxymethyl and $R'_3$ is hydrogen with the proviso that, $R'_2$ is not hydroxymethyl in case $R'_1$ is hydrogen; or $R'_1$ and $R'_2$ together represent a methylene group and $R'_3$ is ethyl, and wherein $n$ is 2, $R'_1$ is an alkaline earth metal, $R'_2$ is hydroxymethyl or alkoxymethyl and $R'_3$ is hydrogen and pharmaceutically acceptable acid addition salts thereof.

* * * * *

Disclaimer 4,070,450.—*Richard Barner*, Witterswil, and *Walter Boguth*, Riehen, Switzerland. SUNSCREENING COMPOUND AND METHOD. Patent dated Jan. 24, 1978. Disclaimer filed June 8, 1978, by the assignee, *Hoffmann-La Roche Inc.*

Hereby enters this disclaimer to claim 16 of said patent.

[*Official Gazette August 1, 1978.*]

UNITED STATES PATENT AND TRADEMARK OFFICE
CERTIFICATE OF CORRECTION

PATENT NO. : 4,070,450
DATED : January 24, 1978
INVENTOR(S) : Rochard Barner and Walter Boguth It is certified that error appears in the above-identified patent and that said Letters Patent are hereby corrected as shown below:

[3d] Foreign Application Priority Data

April 18, 1974 [CH] Switzerland  5357/74

Signed and Sealed this

Eighteenth Day of March 1980

[SEAL]

Attest:

SIDNEY A. DIAMOND

Attesting Officer  Commissioner of Patents and Trademarks